United States Patent [19]
Ott-Dembrowski et al.

[11] Patent Number: 5,847,216
[45] Date of Patent: Dec. 8, 1998

[54] PREPARATION OF SELEGILINE

[75] Inventors: Silvia Ott-Dembrowski, Petershagen; Richard Cyrus, Ludwigshafen; Jörg Schmidt, Minden; Hans Waiblinger, Bad Oeynhausen, all of Germany

[73] Assignee: Knoll Aktiengesellschaft, Ludwigshafen, Germany

[21] Appl. No.: 793,458

[22] PCT Filed: Sep. 2, 1995

[86] PCT No.: PCT/EP95/03460

§ 371 Date: Feb. 27, 1997

§ 102(e) Date: Feb. 27, 1997

[87] PCT Pub. No.: WO96/08461

PCT Pub. Date: Mar. 21, 1996

[30] Foreign Application Priority Data

Sep. 13, 1994 [DE] Germany ............ 44 32 610.6

[51] Int. Cl.$^6$ .................................................. C07C 211/00
[52] U.S. Cl. ............................................................ 564/381
[58] Field of Search ................................................ 564/381

[56] References Cited

U.S. PATENT DOCUMENTS

| | | | |
|---|---|---|---|
| 3,429,922 | 2/1969 | Beregi et al. ............................ | 564/381 |
| 3,485,874 | 12/1969 | Ecsery et al. ........................... | 260/570 |
| 4,156,017 | 5/1979 | Kruger et al. ........................... | 564/381 |
| 4,564,706 | 1/1986 | Ecsery et al. ........................... | 564/376 |
| 5,589,513 | 12/1996 | Magyar et al. ......................... | 514/654 |

FOREIGN PATENT DOCUMENTS

| | | |
|---|---|---|
| 099 302 | 1/1984 | European Pat. Off. . |
| 344 675 | 12/1989 | European Pat. Off. . |
| 393 306 | 3/1962 | Switzerland . |

OTHER PUBLICATIONS

Chemical Abstracts, vol. 105, No. 13, (1986).

MacGregor et al., Journal of Labelled Compounds and Radiopharmaceuticals, vol. 25, No. 1, pp. 1–9 (1988).

Acta Pharm. vol. 62, pp. 201–211 (1992).

*Primary Examiner*—Deborah C. Lambkin
*Attorney, Agent, or Firm*—Keil & Weinkauf

[57] ABSTRACT

A process for preparing selegiline hydrochloride by reaction of R-(−)-N,α-dimethylphenylethylamine with 3-bromo-1-propyne is described, which consists in reacting the substances in a molar ratio of approximately 2:1 at 30°–50° C. in a solvent mixture of an aromatic hydrocarbon and water and isolating the selegiline from the organic phase and converting it into the hydrochloride.

3 Claims, No Drawings

PREPARATION OF SELEGILINE

This application is a 571 of PCT/EP95/03460 filed Feb. 9, 1995.

The present invention relates to a novel process for preparing selegiline.

Selegiline is the (R)-(−)-isomer of deprenyl (=N,α-dimethyl-N-2-propynylphenethylamine), which has the formula

$$C_6H_5-CH_2-CH(CH_3)-N(CH_3)-CH_2-C\equiv CH \quad I.$$

A number of preparation processes, which deal both with the preparation of racemic product and the optical isomers for the synthesis of deprenyl or its antipodes, are known. The starting material used is racemic or optically active N,α-dimethylphenethylamine $[C_6H_5-CH_2-CH(CH_3)-NH-CH_3 \ (=II)]$.

CH Patent 393,306 describes, inter alia, the preparation of racemic deprenyl starting from II with the aid of a metalating agent such as lithium amide or phenylsodium and subsequent alkylation for ten hours in boiling toluene with 3-bromo-1-propyne. Reactions of this type can hardly be carried out on an industrial scale.

According to another chemical process (NL-OS 6,605,956), II can be reacted with propargylaldehyde and the resulting intermediate can be reduced with aluminum amalgam. The disadvantages of this process are the strong tendency of the propargylaldehyde to polymerize under the reaction conditions, and for it to cause severe skin irritation. In addition, mercury and its salts are severe (environmental pollutants, which can only be disposed of at great cost.

The preparation of deprenyl by reaction of α-methylphenylethyl chloride by means of N-methylpropynylamine in a closed tube at 80° C. described in DE-AS 1,227,447 cannot be realized on an industrial scale in practice because of the poor yield and the high costs of the N-methylpropynylamine. The high costs of the reagents employed make the process economically inefficient.

According to DE-AS 1,227,447, II is allowed to react with 1,3-dibromopropene at 100° C. for 7 hours. Unreacted starting material is converted by reaction with benzoyl chloride into N,α-dimethyl-N-benzoylphenethylamine, which is separated from the desired final product. Hydrogen bromide has to be eliminated from the resulting N,α-dimethyl-N-3-bromo-2-propenylphenethylamine under the action of alcoholic/aqueous potassium hydroxide solution in order to obtain the desired propynyl compound. This process is laborious, time-consuming and unsuitable for production on an industrial scale.

Finally, DE-AS 1,227,447 (cf. Example 5) describes the reaction of propargyl bromide with twice the molar amount of N-(1-phenylisopropyl)-methylamino in the absence of a solvent at 100° C. This process does give a relatively good yield, but is not suitable for an industrial-scale synthesis because isolation and purification of the end product are extremely elaborate.

The same goes for the reaction, cited in Acta Pharm. Hung. 1992, 62, 201 (page 204), of N-(1-phenylisopropyl)-methylamine with acetylene in the presence of paraformaldehyde and $CuCl_2$ (AT 252,901). The selegiline has to be purified by distillation in this reaction.

An elaborate purification procedure is also necessary for the selegiline produced in accordance with H. Cabelled Compds. Rodiopharm 1988, 25, 1 (page 7).

EP Patent 99,302 describes the alkylation of (R)-II with 3-bromo-1-propyne in a two-phase binary system of benzene and aqueous alkali at a starting temperature of 60° C. Working at elevated temperature and the use of aqueous sodium hydroxide solution, however, cause problems due to the presence of 3-bromo-1-propyne, eg. ready and increased formation of polymeric products.

According to a further method (EP-OS 344,675), alkylation with 3-bromo-1-propyne is carried out in halogen-containing aliphatic hydrocarbons using potassium carbonate. The alkylating agent and the auxiliary base are used in an excess of at least 10%. The total amount of 3-bromo-1-propyne is added in a single portion or in a time interval of only 5 minutes. The excess and addition of a single portion are unnecessary for the course of the alkylation, since the yields of selegiline hydrochloride are only barely over 50%. Additionally, the use of halogen-containing hydrocarbons, such as chloroform in particular, is not safe from the occupational and environmental points of view because of the carcinogenicity of the solvent.

These known processes are difficult to transfer to a large industrial scale and do not make possible the preparation of selegiline hydrochloride in good yield.

The present invention relates to a process for preparing selegiline hydrochloride by reaction of R-(−)-N,α-dimethylphenylethylamine with 3-bromo-1-propyne, which consists in reacting the substances in a molar ratio of approximately 2:1 at 30°–50° C. in a solvent mixture of an aromatic hydrocarbon and water and in the absence of a catalyst, and isolating the selegiline from the organic phase and converting it into the hydrochloride.

The molar ratio of II to 3-bromo-1-propyne should be such that the amount of II is just adequate to bind the hydrogen bromide formed in the reaction. As a rule, somewhat less than 2 mol of II per mole of 3-bromo-1-propyne are needed for this. An excess of II which may be present after the end of the reaction should be neutralized, preferably using HBr.

The reaction is carried out at 30°–50° C., preferably at 35°–45° C. The reaction is complete, as a rule, after 5 hours. The reaction time can be shortened by cooling.

The reaction temperature is regulated by the rate of addition of the 3-bromopropyne.

The reaction is carried out in a two-phase system of water and an aromatic hydrocarbon such as benzene, toluene, ethylbenzene, o-, m- or p-xylenes or trialkylated benzene, such as mesitylene. Toluene is the best-suited hydrocarbon.

It is important that the bromide ion formed in the course of the alkylation is rapidly bound by the organic base which is present in excess and passes into the aqueous phase as rapidly as possible as an easily soluble salt.

The amount of water in the two-phase system should be over 10%, preferably 20% or more. Amounts of over 30% do not provide any further advantages.

A special feature of the process is that no catalyst is needed.

During the reaction, the selegiline formed passes into the organic phase. After concentrating the organic phase, the residue is taken up in a polar solvent, such as acetone, methyl ethyl ketone or other low molecular weight ketones. The solution is filtered, if desired after addition of active carbon. The hydrochloride is then precipitated using hydrogen chloride.

Further selegiline hydrochloride can be isolated from the mother liquor.

The compound II can be extracted from the aqueous phase after addition of alkali. The compound II can also be used for a further reaction mixture.

The novel process has the advantage that it yields selegiline hydrochloride in very good yield and purity.

Moreover, the process is simple and can be carried out without relatively great cost. Thus, for example, relatively high temperatures are not needed.

EXAMPLE

A 500 ml three-necked flask, provided with a reflux condenser, stirrer and dropping funnel, was flushed with nitrogen, 124 g of (R)-(−)-N,α-dimethylphenylethylamine were introduced and heated to 38°–42° C. while stirring with 160 ml of toluene and 40 ml of water, and 49.3 g of pure 3-bromo-1-propyne were added dropwise with vigorous stirring in the course of 3 h in such a way that the temperature did not exceed 40°–45° C. After addition was complete, the reaction mixture was stirred at 40°–45° C. for a further 5 h to complete the reaction and allowed to cool to room temperature, whereupon 2 phases were formed. After separation of the two phases, the content of unreacted (R)-(−)-N,α-dimethylphenylethylamine in the organic phase was determined, the equivalent amount of hydrobromic acid was added, and the mixture was stirred vigorously for 15 min and then allowed to stand for 15 min. The toluene phase was separated from the aqueous phase and washed twice with 50 ml of water each time. The combined aqueous extracts were collected. The toluene phase was freed completely from water and toluene at 50° C. in vacuo. The residue was dissolved in 300 ml of acetone, treated with 1 g of activated carbon with stirring and filtered in vacuo. 15.1 g of hydrogen chloride gas were passed into the acetone solution at $\leq 30°$ C. while stirring and cooling. A pH of about 2 was established. The reaction mixture was cooled to 20° C. while stirring and stirring was continued for 6 h. The precipitated crystals were filtered off with suction under reduced pressure, washed with 30 ml of acetone and dried at 70° C. in vacuo. 81.7 g of selegiline hydrochloride were obtained, m.p. 142°–145° C.;

$[\alpha]_D^{20}=11.8°/c=10$, water (yield 88%).

About 80% of the solvent were distilled off at normal pressure from the acetone mother liquor of the first crystallizate. After cooling the mother liquor to 20° C. and crystallizing for several hours, a second crystallizate was obtained which was filtered off with suction under reduced pressure, washed with a little acetone and dried in vacuo at 70° C. A further 8 g of selegiline hydrochloride were obtained, which was recrystallized from aqueous acetone with addition of activated carbon. 4.6 g of selegiline hydrochloride were obtained, m.p. 142°–147° C.;

$[\alpha]_D^{20}=12°$ c=10, water (yield 5%).

The combined aqueous solutions were treated with sodium hydroxide solution. The (R)-(−)-N,α-dimethylphenylethylamine was extracted with toluene. The base recovered in this way can be used again for the next batch for the preparation of selegiline hydrochloride.

We claim:

1. A process for preparing selegiline hydrochloride by reaction of R-(−)-N,α-dimethylphenylethylamine with 3-bromo-1-propyne, which comprises reacting the substances in a molar ratio of approximately 2:1 at 30°–50° C. in a solvent mixture of an aromatic hydrocarbon and water in the absence of a catalyst, and isolating the selegiline from the organic phase and converting it into the hydrochloride.

2. The process of claim 1, wherein the reaction is carried out at a temperature of from 35° to 45° C.

3. The process of claim 1, wherein the reaction is carried out at a temperature of from 40° to 45° C.

* * * * *